United States Patent [19]
Altman et al.

[11] Patent Number: 5,662,698
[45] Date of Patent: Sep. 2, 1997

[54] NONSHUNTING ENDOCARDIAL DEFIBRILLATION LEAD

[75] Inventors: Peter A. Altman, San Francisco; William D. Miner, II, Santa Clara; M. Elizabeth Bush, Fremont, all of Calif.

[73] Assignee: Ventritex, Inc., Sunnyvale, Calif.

[21] Appl. No.: 568,034

[22] Filed: Dec. 6, 1995

[51] Int. Cl.$^6$ ............................................. A61N 1/36
[52] U.S. Cl. ............................................. 607/123
[58] Field of Search ............................. 607/122, 123, 607/126, 130

[56] References Cited

U.S. PATENT DOCUMENTS

| | | | |
|---|---|---|---|
| 4,301,815 | 11/1981 | Doring | 607/126 |
| 4,825,871 | 5/1989 | Cansell . | |
| 5,090,422 | 2/1992 | Dahl et al. . | |
| 5,190,052 | 3/1993 | Schroeppel . | |
| 5,250,167 | 10/1993 | Adolf et al. | 204/299 |

OTHER PUBLICATIONS

"A New Method of Single-Lead DDD Stimulation" Frohlich, et al., *IEEE EMBS 1995 Conf. Proceedings*, Montreal.

"Current Concepts for Selecting the Location, Size and Shape of Defibrillation Electrodes" Ideker, et al., *PACE*, vol. 14, Feb. 1991, Part I, pp. 227–240.

"Implantable Cardioverter Defibrillator Lead Technology: Improved Performance and Lower Defibrillation Threshold", Lang, et al., *PACE*, vol. 18, Mar. 1995, Part II, pp. 548–559.

"Finite Element analysis of Cardiac Defibrillation Current Distributions" Sepulveda, et al., *IEEE Transactions on Biomedical Engineering*, vol. 37, No. 4, Apr. 1990, pp. 354–365.

"Electrochemical Muscles: Micromachining Fingers and Corkscrews" Smela, et al., *Adv. Materials*, vol. 5, No. 9, 1993, pp. 630–632.

"Electrostriction of Highly Swollen Polymer Gel: Possible Application for Gel Actuator", Hirai, et al., *Journal of Applied Polymer Science*, vol. 53, 1994, pp. 79–84.

"Electro–Driven Chemomechanical Polymer Gel as an Intelligent Soft Material", Okuzaki, et al., *J. Biomaterial Science, Polymer Edition*, vol. 5, No. 5, 1994, pp. 485–495.

"Continuum Electromechanics of Ionic Polymeric Gels as Artificial Muscles for Robotic Applications", Shahinpoor, *Smart Material Struct.* 3, 1994, pp. 367–372.

*Primary Examiner*—William E. Kamm
*Assistant Examiner*—Scott M. Getzow
*Attorney, Agent, or Firm*—Steven M. Mitchell; M. Elizabeth Bush; Mark J. Meltzer

[57] ABSTRACT

A defibrillation insulating device prevents current from directly shunting through the blood pool from the right ventricular defibrillation electrode to a superior vena cava electrode and vice versa. This forces current to flow through the heart muscle, thus increasing the current density throughout the heart, to depolarize the majority of the cardiac tissue with a minimum of energy.

24 Claims, 9 Drawing Sheets

BEFORE OPENING

OPENING

OPEN

NONSHUNTING ENDOCARDIAL DEFIBRILLATION LEAD

FIELD OF THE INVENTION

The present invention relates generally to cardiac defibrillation devices, and more specifically to an implantable device which provides a means for directing energy to the heart muscle during cardiac atrial or ventricular defibrillation.

BACKGROUND OF THE INVENTION

It is desirable to reduce the size of an implantable cardioverter/defibrillator (ICD) in order to improve patient comfort, reduce risk of erosion through the skin, and facilitate pectoral placement. Because the batteries and capacitors account for a large portion of the defibrillator, reducing the defibrillation threshold (DFT), or the amount of energy required to defibrillate the heart, is key to allowing the device size to be reduced. Internal defibrillation energies are typically between 5 and 40 J, depending on the individual patient and his condition, the lead system, and the defibrillation waveform. Using less energy to defibrillate has the added benefit of improving patient comfort and reducing trauma to the patient's cardiac conduction system.

Many techniques have been used in the past to reduce DFTs. These include the use of modified electrodes, described by Ideker et al. in "Current Concepts for Selecting the Location, Size and Shape of Defibrillation Electrodes," *PACE* 1991, 14:227-240, and described by Lang et at. in "Implantable Cardioverter Defibrillator Lead Technology: Improved Performance and Lower Defibrillation Thresholds," *PACE* 1995, 18:548-559.

SUMMARY OF THE INVENTION

The invention comprises an endocardial defibrillation lead having interelectrode insulation for use during electrical stimulation having the ability to direct energy to the heart muscle while minimizing shunting of current through the blood within the heart chambers. This lead may be used with various combinations of transvenous, epicardial, and subcutaneous electrodes. By substantially limiting energy shunting through the blood pool, the energy required for defibrillation can be minimized.

Endocardial insulation prevents current from flowing in a direct path from a right ventricular (RV) electrode to a superior vena cava (SVC) electrode (and vice versa), forcing more current to pass through the heart muscle, lowering defibrillation thresholds. The system impedance increases with endocardial insulation due to longer current pathways, but more energy is forced through cardiac muscle tissue. In fact, the rise in impedance introduced by the insulation is an indication of the advantage being provided.

The insulation is preferably made of flexible, nonabrasive, biocompatible material, such as silicone rubber laminated with expanded polytetrafluoroethylene (ePTFE), and is of sufficient thickness and dielectric strength to provide adequate electrical insulation from the local potential gradient. The material is provided with a shape so that when implanted within the heart, it partially or fully forms a barrier to minimize or prevent current flow between RV and SVC electrodes through the blood. It preferably is positioned on and extends outwardly from the endocardial lead such that an outer edge of the insulation extends beyond the perimeter of the lead by at least 5 mm continuously for at least 50% of the perimeter of the lead. The material is preferably of a flexible material and sufficiently thin and compliant such that it can extend and collapse with the filling and pumping of the heart. The effectiveness of the device for directing energy to the heart generally increases with increasing coverage of the cross section of the right ventricle.

By directing current flow through the heart muscle with the insulation device, the defibrillation electrode(s) may be reduced in size while maintaining the lower DFT found with larger electrodes. For a transvenously placed lead, this reduction in required surface area may allow the defibrillation electrode diameter to be reduced, so that the lead introducer required to insert the lead through the vein is not increased by the added insulation.

RV and SVC transvenous electrodes are situated in blood, which has nearly three times the conductivity of cardiac muscle. In a discussion of current shunting by the blood during defibrillation between RV and SVC leads, N. G. Sepulveda in "FEA of Cardiac Defibrillation Current Distribution," *I.E.E.E. Biomed. Trans.*, Vol. 37, No. 4, Apr. 1990, approximates the amount of current shunted at nearly 50 percent from finite element analysis studies. This large waste of energy may be drastically reduced using the present invention by introducing a component on a transvenous lead that is designed to reduce the cross sectional area of blood that provides current pathways open to shunting. Sepulveda et at. state, "When blood resistivity is increased, more current tends to flow through the myocardium, rather than going into the chambers leading to higher myocardial voltage gradients." Introduction of a flexible, biocompatible insulative barrier between the RV and SVC electrodes in the blood pool would drastically increase the effective impedance through the blood, and more of the energy would be forced through the desired tissue.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
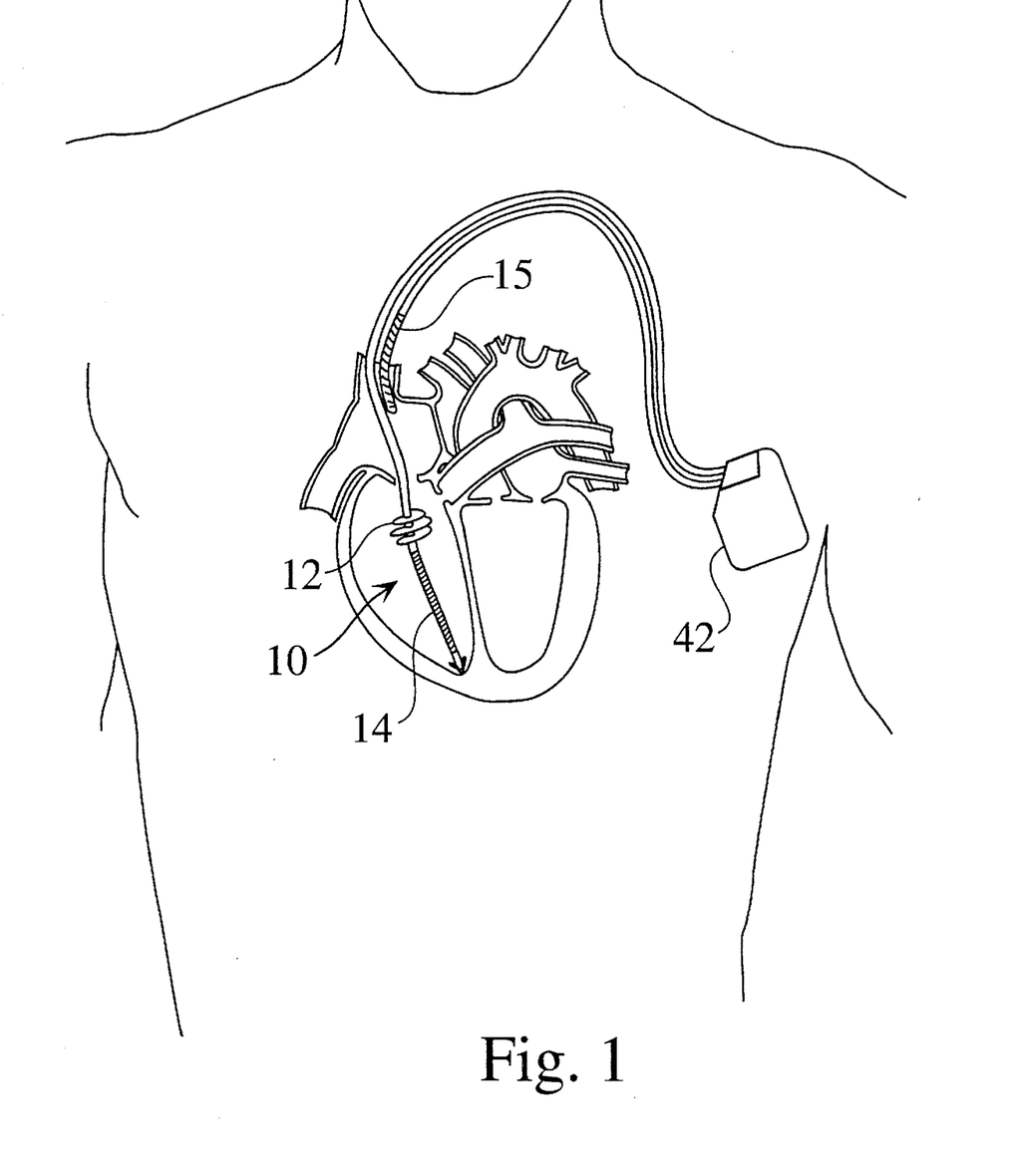
FIG. 1 shows a lead of the present invention having tapered spiral insulation in position in the right ventricle of a patient's heart.

FIG. 1 shows a cylindrical transvenous defibrillation lead 10 having insulation 12 in position in the endocardial space of a patient's heart to reduce blood pool shunting. Defibrillation thresholds are lowered by limiting the amount of current shunting through the blood by creating flexible implantable electrical barriers in this region. The insulation material is biocompatible, flexible, and nonabrasive, and may be impregnated with drugs to reduce tissue response to the material. The material may simply be silicone rubber, or may be a composite material such as 75 to 100 μm thick silicone rubber sandwiched between two 25 μm thick expanded polytetrafluoroethylene (ePTFE) layers which may be impregnated with a hydrogel or with a drug such as the steroid dexamethasone sodium phosphate. The silicone layer provides a current insulating barrier, while the ePTFE minimizes fibrotic growth. Other examples of drugs which may elute from the insulation into the bloodstream and to adjacent tissues such as the endocardium include any suitable drug or combination of drugs intended to counter thrombus formation, fibrosis, inflammation, poor myocardial perfusion, ischemia, arrhythmias, or any combination of these.

The right ventricle and right atrium of the heart are shown, with the tricuspid valve between them. Insulation 12 is in the shape of a spiral, which allows blood to flow past it, while not allowing current to flow directly from the RV electrode to the SVC electrode. Because blood can flow along the spiral, it is not imperative that the spiral be completely flexible. The spiral is preferably only one to three turns in order to allow the defibrillation electrode to be as long as possible without interfering with the tricuspid valve. The spiral may be positioned off center with respect to the electrode in order to position the electrode off center, such as against the septum in the right ventricle. To complete the defibrillation electrode system, a superior vena cava (SVC) electrode 15 is positioned in or near the SVC. Additionally, a subcutaneous electrode may be used, such as an electrode formed by an electrically active pulse generator housing 42.

Figure 5:
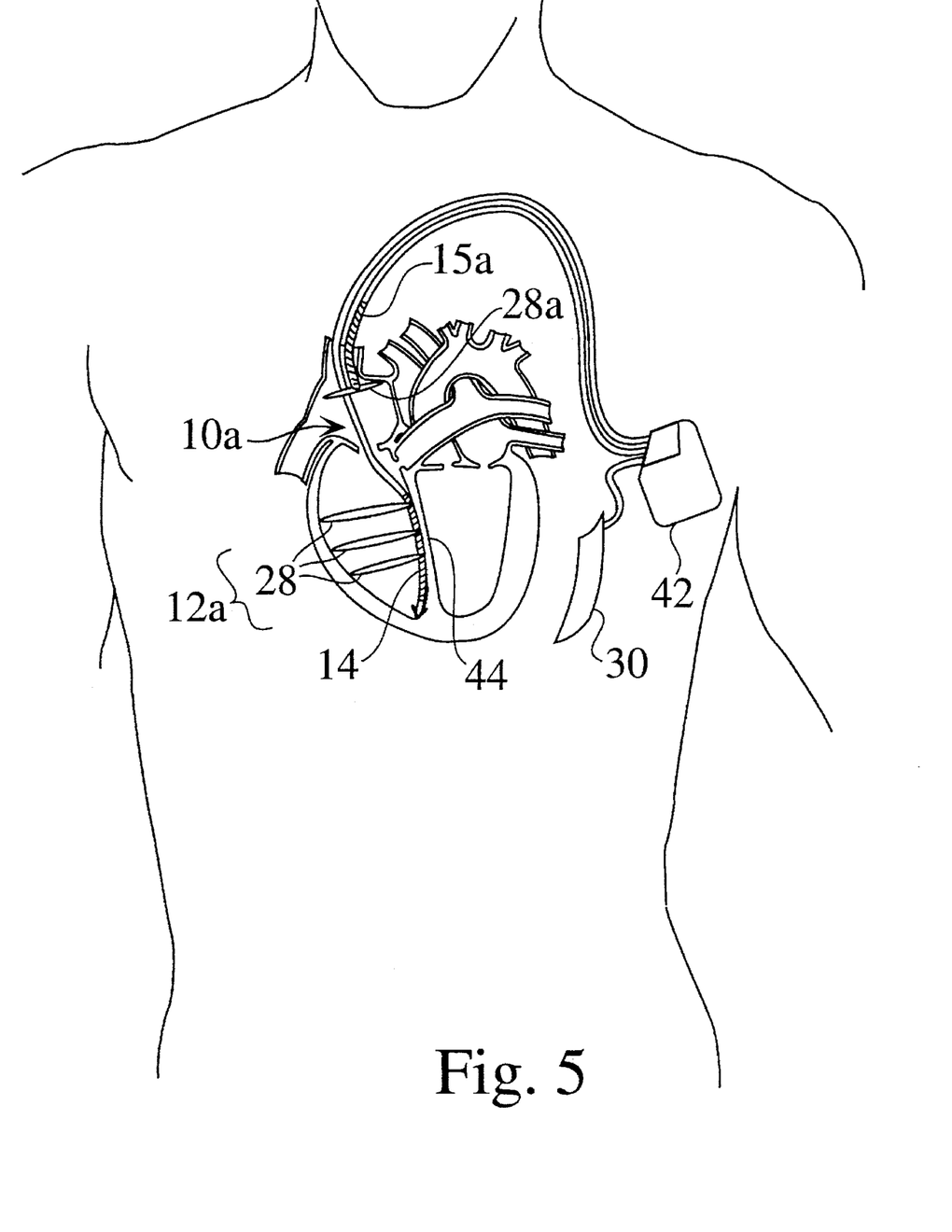
FIG. 5 shows RV and SVC leads of the present invention having insulative disks.
Figure 6:
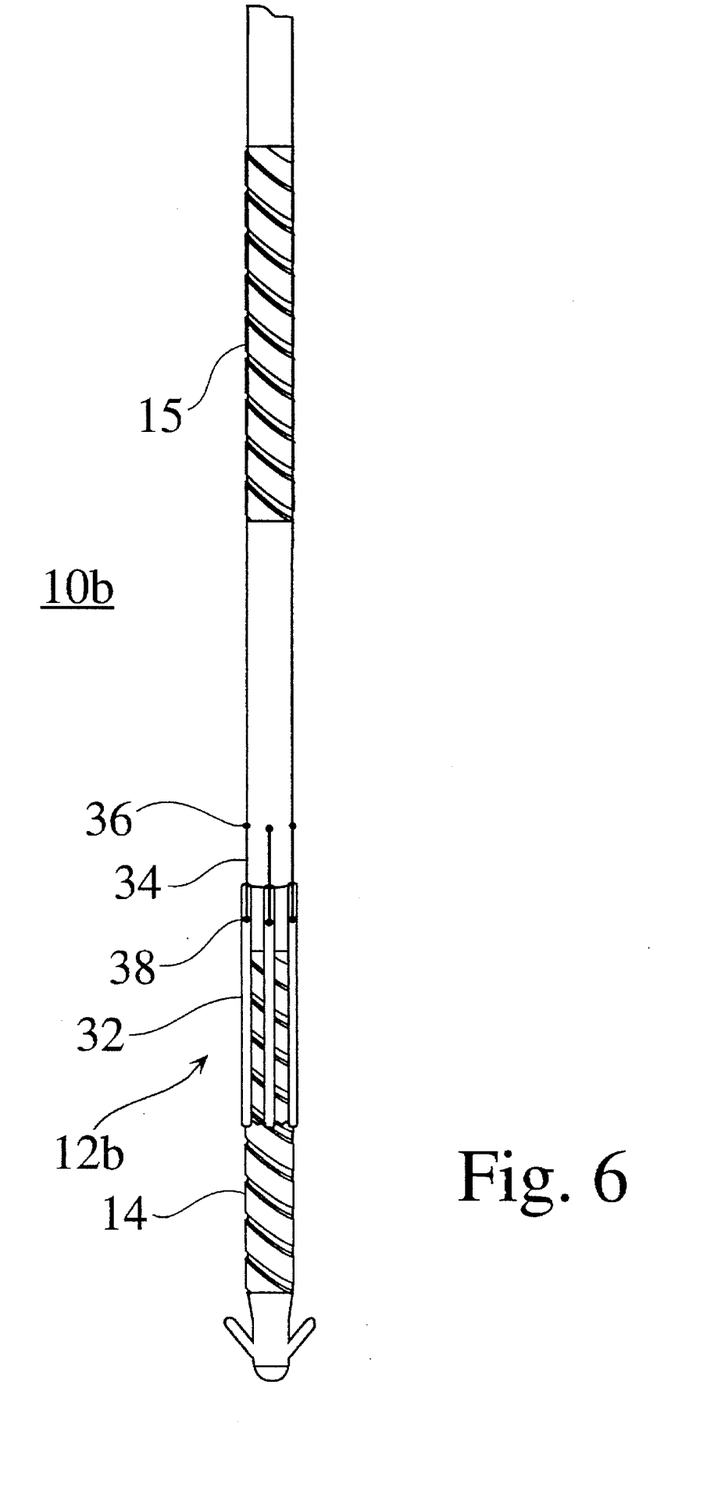
FIGS. 6 and 7 show a lead of the present invention having insulation that is deployable during a defibrillation shock.
Figure 7:
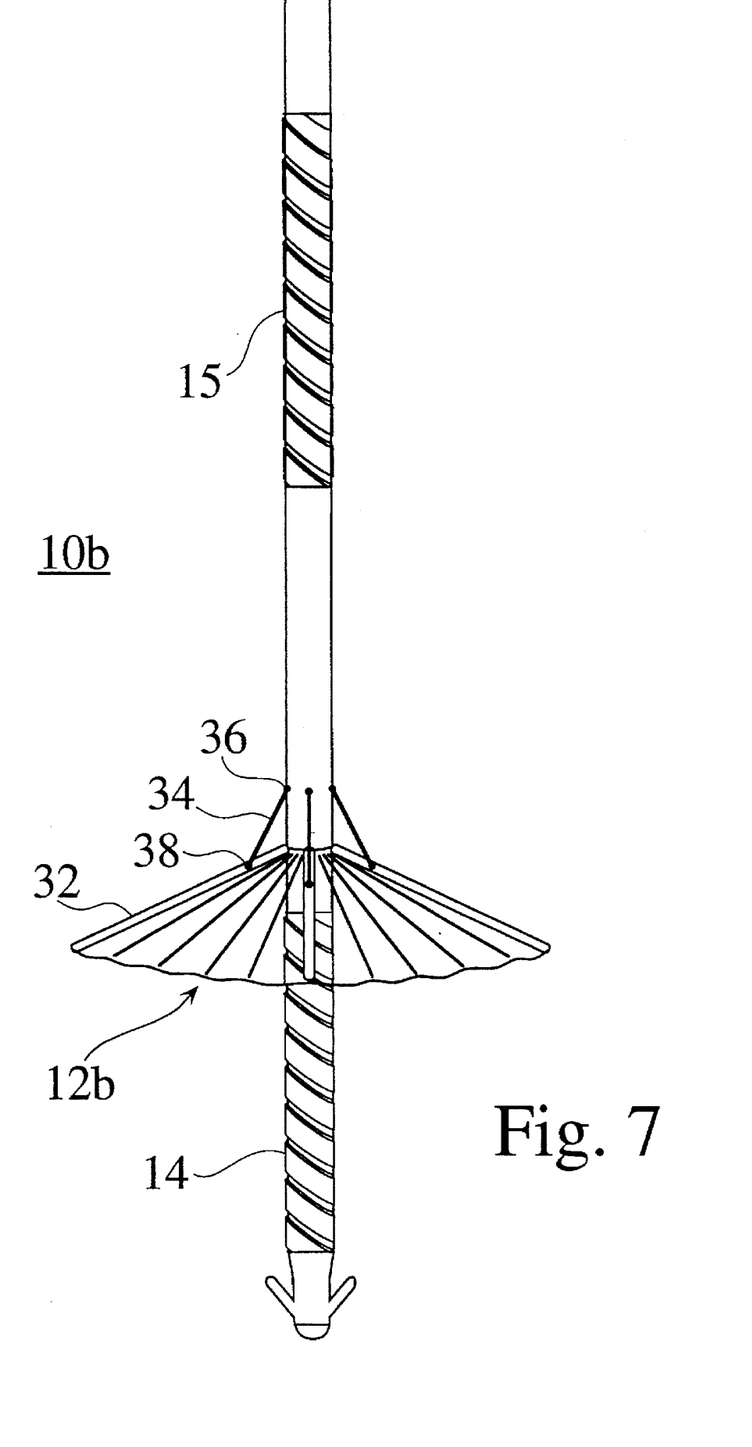

The inventive lead shown includes an RV defibrillation electrode 14, with the insulation 12 located proximal to the RV electrode 14. Alternatively, the inventive lead may include an SVC electrode 15a, in which case the insulation 12 is located distal to the SVC electrode, as shown in FIG. 5. As another alternative embodiment, the inventive lead may include both RV and SVC defibrillation electrodes, in which case, the insulation 12 is located between the two electrodes, as shown in FIGS. 6 and 7.

Insulation 12 is in its collapsed state during insertion, and can be expanded following insertion, and collapsed again for explantation. It is preferred that the insulation be permanently collapsible, or at least flexible, since an uncollapsible, rigid structure could damage the tricuspid valve or other structures during explantation, if required.

Figure 2:
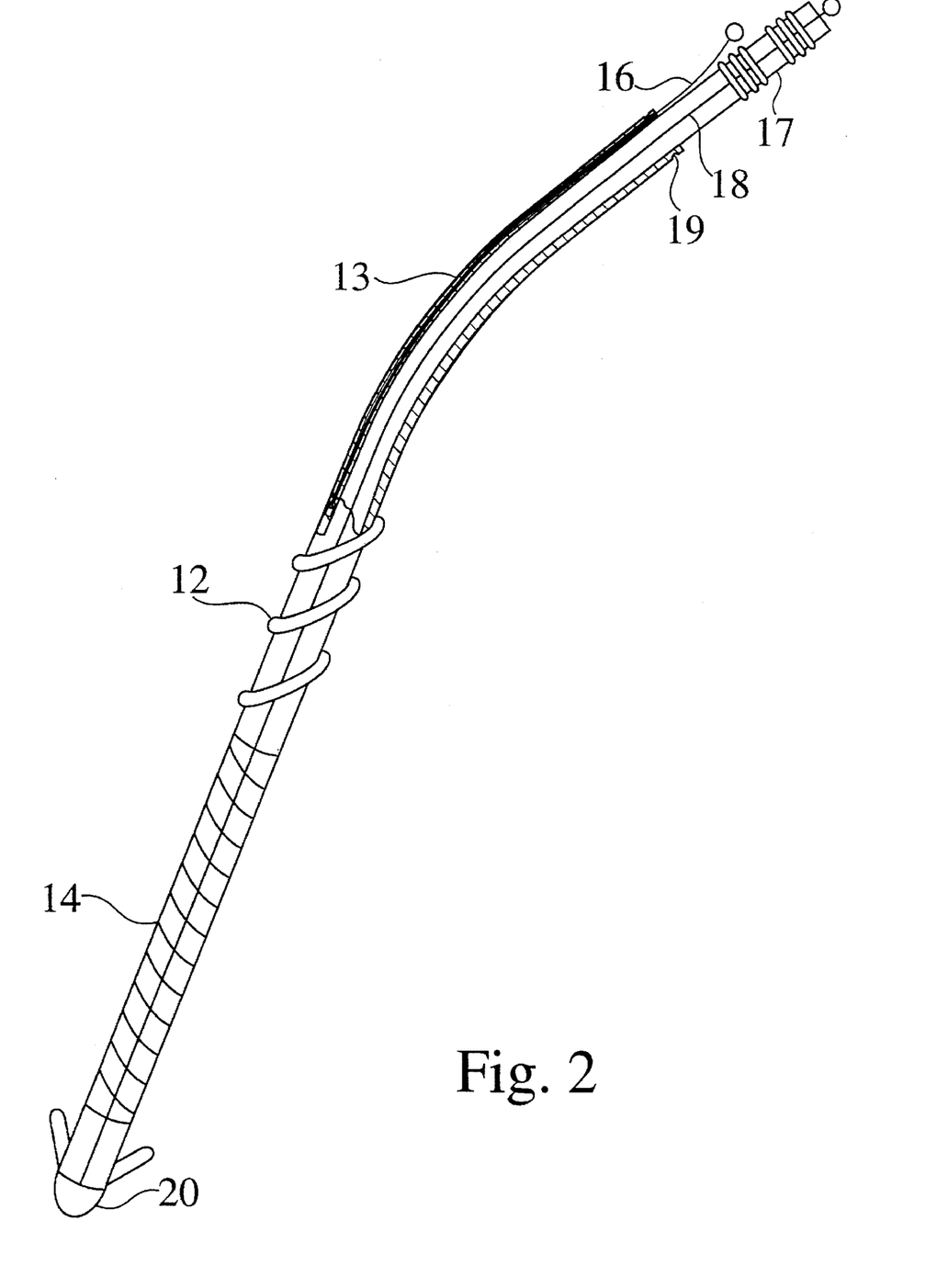
FIG. 2 is a partly cutaway view of the lead of FIG. 1 ready for implantation.

FIG. 2 shows the lead of FIG. 1 in position ready for implantation or explantation. The insulation 12 is positioned on the lead 10 proximal to the RV electrode 14 and is shown with a locking stylet 16 inserted in a lumen within a sheath 13 that is continuous with insulation 12, and pulling insulation 12 toward the connector end 17 to collapse insulation 12 to a small diameter for insertion through a vein. After positioning within the right ventricle, insulation 12 is expanded to a larger diameter by sliding or by sliding and rotating the insulation 12 toward the distal end 20 with locking stylet 16. Locking stylet 16 can be secured to insulation 12 using threads or other means familiar to those knowledgeable in the art of lead design, such that forces and torques may be transmitted to insulation 12. A ligature may be tied around suture groove 19 in sheath 13 to secure insulation 12 in position with respect to the rest of the lead. A locking stylet also is used to apply force to collapse the insulation to a smaller diameter at explant. For both insertion and extraction, a second stylet 18 is advanced all the way to the distal end 20 of the lead to limit the load being transmitted to the myocardium during the insulation collapsing and expanding procedures.

Alternatively, the insulation can be inserted along with the lead into the appropriate location through an introducer using a similar technique as that used to introduce a standard defibrillation electrode. The normal unstressed state of insulation 12 is extending outwardly from the lead body to conform to the chamber. However, the material may be sufficiently compliant that during normal blood flow, the insulation collapses down along the lead body, or flutters freely within the chamber, allowing normal blood movement through the chamber. When the blood is not flowing, such as during ventricular fibrillation (VF), the insulation expands outwardly to prevent current shunting during defibrillation.

In addition, the helical (constant radius) or spiral (varying radius) geometry is used to allow for easy collapse to minimize hydraulic resistance, while simultaneously introducing high electrical impedance in the blood pool by providing a number of barriers over a distance in the right ventricle. The insulation 12 is preferably of varying radius to allow optimal filling of the RV.

Several sizes may be offered to provide optimal fit to the patient's heart. Alternatively, the material may be manufactured larger than intended for implant, to be trimmed to fit the heart by the implanting physician. If the path of greatest current shunt is identifiable, insulation 12 may be made smaller to interrupt only this path. By making the endocardial insulation smaller, the surgery to implant it will be less invasive.

The principal advantage of the insulation is that it forces current through the heart muscle, thus increasing the current density and energy throughout the heart muscle, to depolarize the greatest amount of cardiac tissue at the lowest possible voltage.

Figure 3:
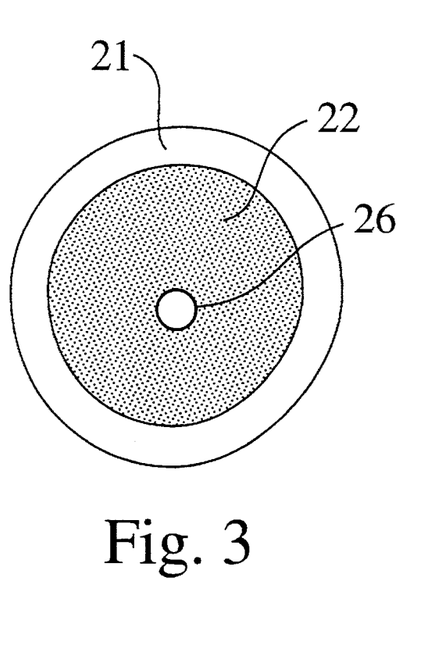
FIGS. 3 and 4 show a cross section of the blood pool within the right ventricle, having a lead with and without endocardial insulation.

In FIG. 3, the right ventricle 21 is shown in cross section, having a cross section of blood 22 available for current shunting using a conventional lead 26 having no additional insulation to prevent current shunting.

Figure 4:
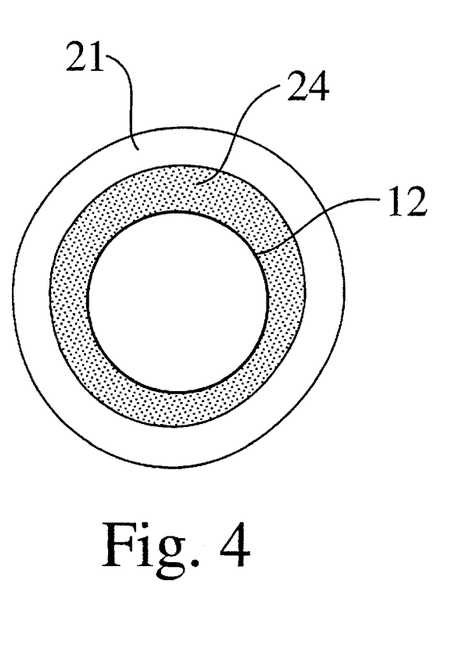

In FIG. 4, the right ventricle 21 is shown in cross section, having a cross section of blood 24 available for current shunting using a lead of the present invention having insulation 12 acting as a barrier to prevent current shunting. Current can still flow through blood between two electrodes, but it must follow a path that goes around the insulative barrier.

FIG. 5 shows an alternative embodiment of the invention. Lead 10a has insulation 12a in the form of one or more disks 28. The disks can be positioned on the lead body proximal to the RV electrode as in the previous embodiment, or they may be placed along the RV electrode itself. One advantage gained when the disks are positioned along the RV electrode itself is that the defibrillation electrode is not shortened, and there is no interference with the tricuspid valve. This disk arrangement is particularly useful when used with a subcutaneous electrode (SQ) such as a patch 30 or electrically active pulse generator housing when it is desirable to direct more current between RV and SQ than between RV and SVC. This disk arrangement allows current to flow approximately perpendicular to the RV electrode, and thus in a substantially direct path from the RV electrode to the SQ electrode.

The insulation is shown positioned off center with respect to the electrode in order to position the electrode off center in the right ventricle, such as against the septum 44 to provide higher current density at the septum. Alternatively, the disks may be centered with respect to the electrode and lead body.

A deployment mechanism may be used to deploy the disks, such as that described for deploying an electrode in U.S. Pat. No. 5,190,052 to Schroeppel which is incorporated herein by reference in its entirety. During implant, insulation 12a may be held in place against the lead body by a soluble or biodegradable material.

SVC electrode 15a is shown on a separate lead from lead 10a, and has an insulative disk 28a located distal to the electrode 15a.

FIGS. 6 and 7 show a defibrillation lead 10b having insulation 12b that is deployed only during the delivery of a defibrillation shock. In its deployed condition (FIG. 7), insulation 12b may cover substantially all of the cross section of the right ventricle, since it is only deployed during the shock, and thus, will not obstruct blood flow. The deployment mechanism may use artificial muscle technology, as described in copending U.S. patent application, Ser. No. 08/568,046 which is assigned to the assignee of the present invention; in U.S. Pat. No. 5,250,167 to Adolf et al.; in Hirai et al., "Electrostriction of Highly Swollen Polymer Gel: Possible Application for Gel Actuator," *Journal of Applied Polymer Science*, Vol. 53, 79–84 (1994); in Okuzaki et at., "Electro-driven Chemomechanical Polymer Gel as an Intelligent Soft Material," *J. Biomater. Sci. Polymer Edn*, Vol. 5, No. 5, pp. 485–495 (1994); and in Shahinpoor, "Continuum Electromechanics of Ionic Polymeric Gels as Artificial Muscles for Robotic Applications," *Smart Mater. Struct.* 3,(1994) 367–372; all of which are incorporated herein by reference. Insulation 12b includes pivoting struts 32 which are normally in a position parallel to the lead body and to electrode 14, as shown in FIG. 6. Artificial muscle elements 34 are mechanically coupled to fixed attachment points 36 on lead 10b and to pivoting struts 32 at attachment points 38. When the pulse generator is charging its capacitor(s) to deliver a high voltage defibrillation shock, it applies a voltage across the artificial muscle elements 34 to contract, thereby deploying the electrical insulation 12b to form a barrier to direct current flow to the heart during the shock. Upon successful completion of the shock delivery, the insulation 12b is collapsed using a return spring or by reversing the polarity of the applied voltage to allow for normal function of the heart and normal blood flow. As in the other embodiments described, the insulation may be positioned off center with respect to the electrode in order to position the electrode off center in the right ventricle, such as against the septum.

Insulation 12b may be deployed manually following implantation during defibrillation threshold (DFT) testing. Typically, during DFT testing, a defibrillator is used that is not implantable, and may not have the capability of deploying the insulation. Therefore, the ability to manually deploy the insulation is useful.

Figure 8:
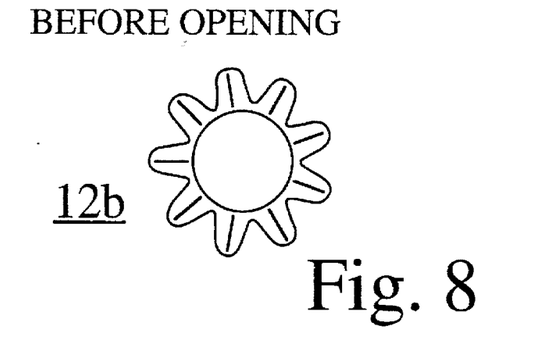
FIGS. 8, 9, and 10 show the insulation before, during, and after deployment.
Figure 9:
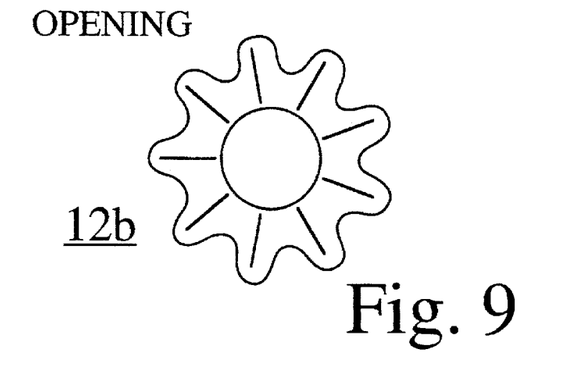
Figure 10:
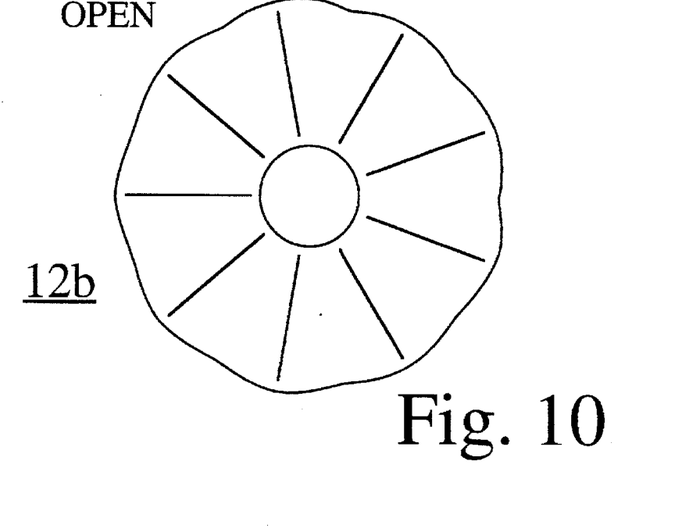

FIGS. 8, 9, and 10 show the insulation 12b of FIGS. 6 and 7 before opening, during opening, and fully open, respectively.

Figure 11:
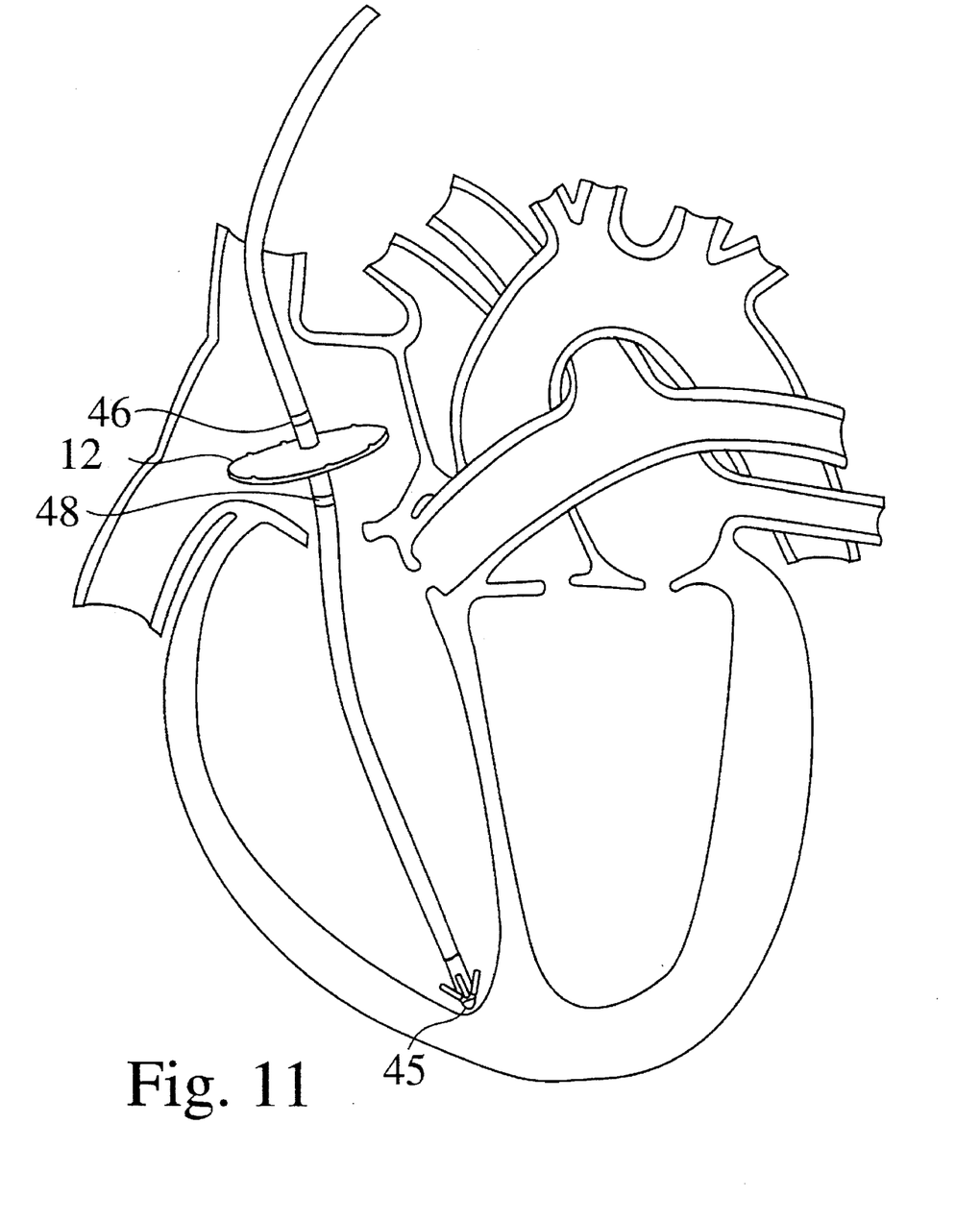
FIG. 11 shows the endocardial insulation used to reduce pacing thresholds.

FIG. 11 shows another use for endocardial insulation 12. In a recent poster presented at the 1995 IEEE Engineering in Medicine and Biology 17th Annual Conference and 21st Canadian Medical and Biological Engineering Conference, Montreal, Canada, Sep. 20–23, 1995, entitled "A New Method of Single-Lead DDD Stimulation," authors Fröhlich and Riedmüller, et al. describe low pacing thresholds from floating atrial electrodes. For such floating electrodes, their close placement in the blood pool results in large losses due to shunting. Pacing thresholds from such electrodes may be lowered by using insulation to limit energy lost by shunting through the blood. By positioning insulation 12 between two floating atrial sense/pace electrodes 46 and 48, the gradient in the atrium is increased to reduce atrial pacing thresholds.

In addition, the small size of the floating atrial electrodes results in very large near field impedances causing most of the energy to be lost to the blood very near the surface of the electrodes. Using larger surface area electrodes such as those used for defibrillation would help reduce these losses.

Figure 12:
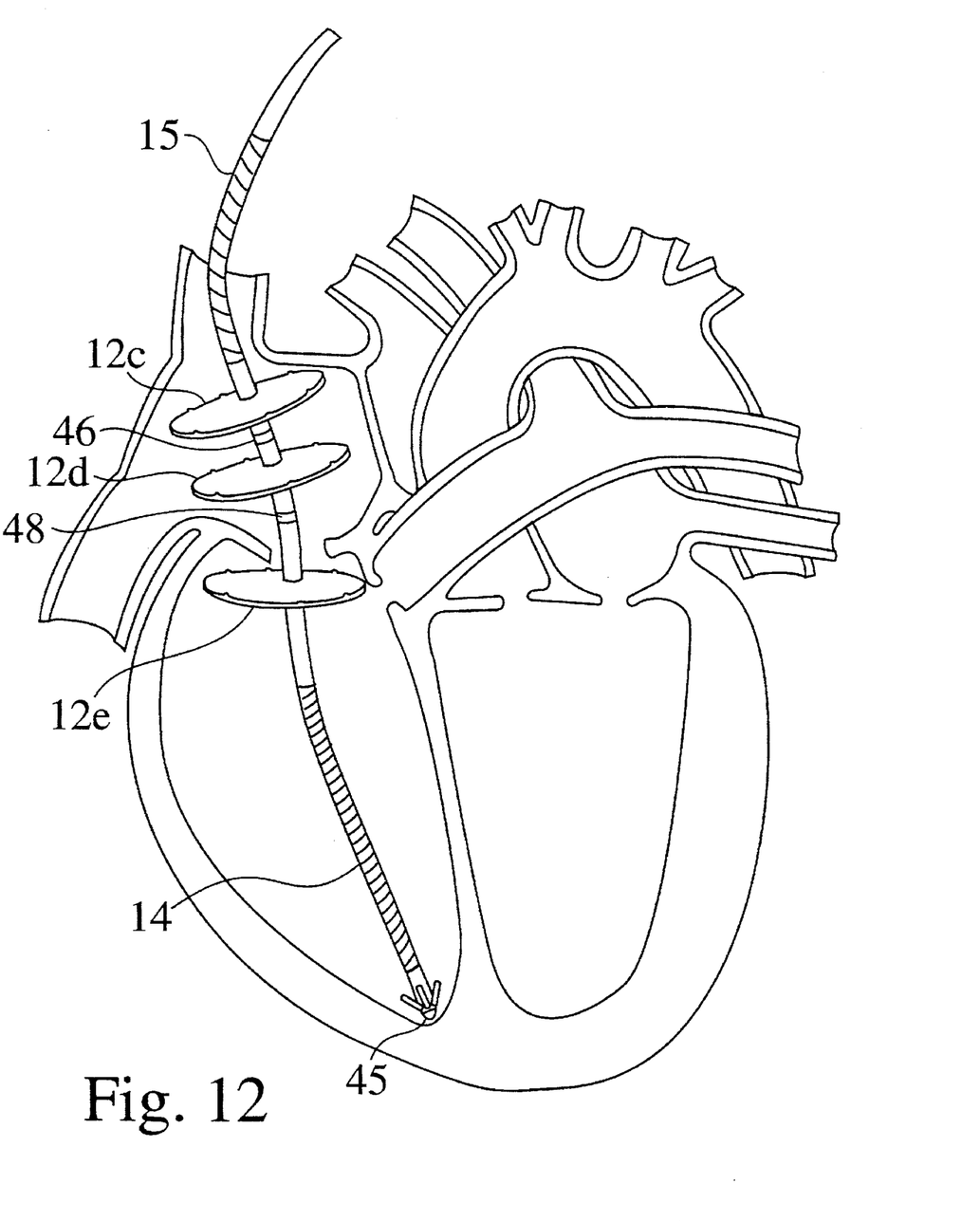
FIG. 12 shows a lead having two atrial sense/pace electrodes, two defibrillation electrodes, a ventricular pacing electrode, and three endocardial insulators located between electrodes.

FIG. 12 shows a defibrillation lead having atrial sense/pace electrodes 46 and 48, an SVC defibrillation electrode 15, an RV defibrillation electrode 14, and a sense/pace electrode 45. Such a lead is described in copending U.S. patent application Ser. No. 08/177,293 to Ben Pless et al., which is assigned to the assignee of the present invention and is incorporated herein by reference in its entirety. Endocardial insulator 12c is positioned between SVC defibrillation electrode 15 and atrial sense/pace electrode 46; endocardial insulator 12d is positioned between atrial sense/pace electrodes 46 and 48; and endocardial insulator 12e is positioned between atrial sense/pace electrode 48 and RV defibrillation electrode 14. For defibrillation, endocardial insulators between two defibrillation electrodes will reduce defibrillation thresholds. For pacing, endocardial insulators between two electrodes used for pacing will reduce pacing thresholds. Note that either SVC defibrillation electrode 15 or RV defibrillation electrode 14 may be used to form a bipolar pair with atrial sense/pace electrode 46 or 48. Using the larger defibrillation electrodes will reduce large losses associated with near field impedances. Note also that any combination of endocardial insulators 12c, 12d, and 12e may be used to achieve the desired goal.

It should be understood that various alternatives to the embodiments of the invention described herein may be employed in practicing the invention. For example, endocardial insulation may be used to decrease current shunting during atrial defibrillation, improve specificity of endocardial mapping techniques, and improve sensing of cardiac electrical activity in transvenous pacing leads. In addition, small strain gauges may be incorporated into the endocardial insulation to sense heart motion. It is thus intended that the following claims define the scope of the invention and that structures and methods within the scope of these claims and their equivalents be covered thereby.

What is claimed is:

1. An endocardial lead having a device for steering current between a first electrode and a second electrode, wherein said first electrode is positioned on said endocardial lead, said device comprising:

electrical insulation positioned on and extending outwardly from said endocardial lead such that an outer edge of said insulation extends beyond a perimeter of the endocardial lead by at least 5 mm continuously for at least 50% of said perimeter of said lead, and positioned between said first and second electrodes, and being capable of interrupting a current path between said first electrode and said second electrode.

2. The device of claim 1, wherein said first electrode and said second electrode are electrodes for cardiac defibrillation.

3. The device of claim 1, wherein said first electrode is a sense/pace electrode.

4. The device of claim 1, wherein said insulation is manufactured larger than intended for implant and comprises a material that can be trimmed by a physician during implant.

5. The device of claim 1, wherein said insulation comprises a flexible material which is sufficiently compliant to extend and collapse with heart and blood motion.

6. The device of claim 1, wherein said insulation comprises silicone rubber or silicone rubber laminated to ePTFE.

7. The device of claim 1, wherein said insulation is in a shape selected from the group consisting of a helix, a spiral, and one or more disks.

8. The device of claim 1, wherein said insulation is impregnated with a therapeutic drug.

9. An implantable endocardial cardiac lead comprising:
   a lead body;
   at least one defibrillation electrode; and
   electrical insulation for directing defibrillation electrical energy to a patient's heart, said insulation being positioned on said lead and extending outwardly from said lead body such that an outer edge of said insulation extends beyond a perimeter of said lead body by at least 5 mm continuously for at least 50% of said perimeter of said lead body, and positioned between said first and second electrodes, and being capable of interrupting a direct current path between said at least one defibrillation electrode and a second defibrillation electrode.

10. The lead of claim 9, wherein said insulation is in a shape selected from the group consisting of a helix, a spiral, and one or more disks.

11. The lead of claim 9, wherein said defibrillation electrode has a proximal end and a distal end, wherein said insulation is in the shape of at least one disk, and wherein said at least one disk is positioned on said lead between said proximal and distal ends of said defibrillation electrode.

12. The lead of claim 9, wherein said insulation is manufactured larger than intended for implant and comprises a material that can be trimmed by a physician prior to implant to fit said patient's heart for optimizing prevention of shunting of the current.

13. The lead of claim 9, wherein said insulation comprises a flexible material which is sufficiently compliant to extend and collapse with heart and blood motion.

14. The lead of claim 9, wherein said insulation is deployable.

15. The lead of claim 14, and further including at least one artificial muscle element mechanically coupled to said insulation such that application of voltage across said artificial muscle element causes said insulation to deploy.

16. The lead of claim 9, wherein said insulation is positioned off center with respect to said electrode whereby a first side of said electrode has more insulation than a second side of said electrode.

17. A method for implanting the lead of claim 16 in a patient, comprising the steps of:
   (a) inserting said electrode through a vein and into the patient's right ventricle; and
   (b) orienting said lead such that said electrode second side faces the patient's intraventricular septum.

18. An implantable endocardial cardiac lead comprising:
   a lead body;
   at least one defibrillation electrode; and
   electrical insulation having a convex outer perimeter, and positioned on and extending outwardly from said lead body such that the distance from said lead body to a first point on said outer perimeter is shorter than the distance from said lead body to a second point on said outer perimeter, and positioned between said first defibrillation electrode and a second defibrillation electrode, and being capable of interrupting a direct current path between said first and second defibrillation electrodes.

19. A method for implanting the lead of claim 18 in a patient, comprising the steps of:
   (a) inserting said at least one defibrillation electrode through a vein and into the patient's right ventricle; and
   (b) rotating said lead such that said first point on said electrical insulation outer perimeter contacts the patient's intraventricular septum.

20. A cardiac stimulation system for implantation in a patient's body, including:
   a pulse generator for generating defibrillation electrical energy;
   at least one defibrillation lead electrically attached to said pulse generator, said at least one defibrillation lead comprising a lead body, at least one defibrillation electrode, and an electrically insulative portion extending outwardly from said lead body such that an outer edge of said insulation extends beyond the perimeter of said lead body by at least 5 mm continuously for at least 50% of the perimeter of said lead body and having a dielectric strength sufficient to prevent blood shunting of at least a portion of said defibrillation electrical energy.

21. The cardiac stimulation system of claim 20, wherein said at least one defibrillation electrode is an endocardial right ventricular defibrillation electrode, and wherein said insulation is located proximal to said right ventricular defibrillation electrode.

22. The cardiac stimulation system of claim 20, wherein said at least one defibrillation electrode includes a superior vena cava defibrillation electrode, and wherein said insulation is located distal to said superior vena cava defibrillation electrode.

23. The cardiac stimulation system of clam 20, wherein said at least one defibrillation electrode includes a first and a second defibrillation electrode, and wherein said insulation is positioned on said lead body between said first and second defibrillation electrodes.

24. The cardiac stimulation system of claim 20, and further comprising:
   control means for sensing an arrhythmic episode requiring therapeutic electrical pulses and for supplying a voltage across an artificial muscle element to deploy said insulation during said episode and for causing said pulse generator to generate said therapeutic electrical pulses through said at least one defibrillation electrode.

* * * * *